United States Patent

Leppard et al.

Patent Number: 5,472,992
Date of Patent: Dec. 5, 1995

[54] PHOTOPOLYMERIZABLE COMPOSITIONS CONTAINING AN ALKYLBISACYLPHOSPHINE OXIDE

[75] Inventors: David G. Leppard, Marly, Switzerland; Manfred Köhler, Freiburg, Germany; Ljubomir Misev, Allschwil, Switzerland

[73] Assignee: Ciba-Geigy Corporation, Ardsley, N.Y.

[21] Appl. No.: 234,887

[22] Filed: Apr. 28, 1994

Related U.S. Application Data

[62] Division of Ser. No. 947,653, Sep. 17, 1992, Pat. No. 5,399,770.

[30] Foreign Application Priority Data

Sep. 23, 1991 [CH] Switzerland ............... 2809/91
Nov. 14, 1991 [CH] Switzerland ............... 3322/91

[51] Int. Cl.$^6$ ............... C08F 2/50; C08F 4/00; C08K 3/22; C08L 67/07
[52] U.S. Cl. ............... 522/18; 522/64; 522/28; 522/81; 522/107
[58] Field of Search ............... 522/64, 18, 28, 522/8, 81, 107

[56] References Cited

U.S. PATENT DOCUMENTS

| | | | |
|---|---|---|---|
| 3,668,093 | 6/1972 | Rettig | 204/159.23 |
| 4,737,593 | 4/1988 | Ellrich et al. | 568/15 |
| 4,792,632 | 12/1988 | Ellrich et al. | 568/15 |
| 4,868,091 | 9/1989 | Boettcher et al. | 430/281 |
| 4,922,004 | 5/1990 | Köhler et al. | 560/221 |

FOREIGN PATENT DOCUMENTS

| | | |
|---|---|---|
| 0184095 | 6/1986 | European Pat. Off. |
| 0209831 | 4/1987 | European Pat. Off. |
| 0262629 | 4/1988 | European Pat. Off. |
| 0413657 | 2/1991 | European Pat. Off. |
| 0495752 | 7/1992 | European Pat. Off. |

OTHER PUBLICATIONS

Chem. Abst. of EP 413,657 (91-052929/08).

*Primary Examiner*—Susan W. Berman
*Attorney, Agent, or Firm*—Michele A. Kovaleski; Luther A. R. Hall

[57] ABSTRACT

Compounds of the formula I

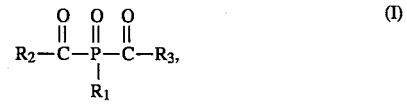

in which $R_1$ is $C_1$–$C_{18}$alkyl, cyclopentyl or cyclohexyl, and $R_2$ and $R_3$, independently of one another, are phenyl which is unsubstituted or monosubstituted to tetrasubstituted by halogen, $C_1$–$C_4$alkyl and/or $C_1$–$C_4$alkoxy, with the proviso that $R_1$ is not decyl if $R_2$ and $R_3$ are chlorine-substituted phenyl, are suitable for the photopolymerisation of compounds containing ethylenically unsaturated double bonds.

15 Claims, No Drawings

PHOTOPOLYMERIZABLE COMPOSITIONS CONTAINING AN ALKYLBISACYLPHOSPHINE OXIDE

This is a divisional of Ser. No. 07/947,653, filed Sep. 17, 1992, now U.S. Pat. No. 5,399,770.

The invention relates to bisacylphosphine oxide photoinitiators and to compositions which contains these photoinitiators.

Mono- and bisacylphosphine oxides are known as photoinitiators. EP-A-184 095 describes bisacylphosphine oxides which are used as photocuring agents for dental compositions. EP-A-262 629 discloses the use of bisacylphosphine oxides in compositions which can be developed in aqueous-alkaline media for the production of printing plates and relief forms. Further mono- and bisacylphosphine oxide photoinitiators are disclosed in EP-A-413 657.

For the extensive range of applications of photoinitiators, there continues to be a demand for effective photoinitiators which are easy to prepare.

It has been found that certain bisacylphosphine oxide compounds containing alkyl radicals on the phosphorus are effective photoinitiators.

The invention thus relates to compounds of the formula I

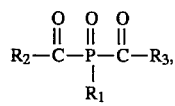

in which $R_1$ is $C_1$–$C_{18}$alkyl, cyclopentyl or cyclohexyl, and $R_2$ and $R_3$, independently of one another, are phenyl which is unsubstituted or monosubstituted to tetrasubstituted by halogen, $C_1$–$C_4$alkyl and/or $C_1$–$C_4$alkoxy, with the proviso that $R_1$ is not decyl if $R_2$ and $R_3$ are halogen-substituted phenyl.

$C_1$–$C_{18}$Alkyl $R_1$ may be linear or branched and is, for example, methyl, ethyl, n-propyl, isopropyl, n-butyl, isobutyl, sec-butyl, tert-butyl, pentyl, hexyl, heptyl, octyl, 2,4,4-trimethylpent-1-yl, 2-ethylhexyl, nonyl, decyl, dodecyl, or octadecyl.

$R_2$ and $R_3$ as phenyl which is monosubstituted to tetrasubstituted by halogen, $C_1$–$C_4$alkyl and/or $C_1$–$C_4$alkoxy are, for example, chlorophenyl, dichlorophenyl, tetrachlorophenyl, tolyl, dimethylphenyl, mesityl, tetramethylphenyl, ethylphenyl, diethylphenyl, triethylphenyl, methylethylphenyl, dimethylethylphenyl, methoxyphenyl, dimethoxyphenyl, trimethoxyphenyl, dimethoxymethylphenyl, methoxymethylphenyl, dimethylmethoxyphenyl, ethoxyphenyl, diethoxyphenyl, diethoxymethylphenyl, propyloxyphenyl, butoxyphenyl, dibutoxyphenyl, butoxymethoxyphenyl, ethoxymethoxyphenyl or butoxyethoxyphenyl, preferably mesityl and dimethoxyphenyl.

$R_2$ and $R_3$ are phenyl which is monosubstituted to tetrasubstituted, preferably monosubstituted to trisubstituted, in particular disubstituted or trisubstituted, by halogen, $C_1$–$C_4$alkyl and/or $C_1$–$C_4$alkoxy.

Halogen is fluorine, chlorine, bromine or iodine, in particular chlorine.

Preference is given to compounds of the formula I in which $R_2$ and $R_3$ are identical.

Interesting compounds of the formula I are those in which $R_1$ is $C_1$–$C_{18}$alkyl, for example $C_1$–$C_{12}$alkyl, in particular $C_1$–$C_8$alkyl, or cyclohexyl, and $R_2$ and $R_3$ are phenyl which is substituted by chlorine, $C_1$–$C_4$alkyl and/or $C_1$–$C_4$alkoxy.

Important compounds of the formula I are those in which $R_1$ is cyclopentyl, cyclohexyl, $C_1$–$C_8$alkyl or $C_{12}$–$C_{18}$alkyl, and $R_2$ and $R_3$ are halogen-substituted phenyl.

Further interesting compounds of the formula I are those in which $R_1$ is $C_4$–$C_8$alkyl or cyclohexyl.

Other preferred compounds of the formula I are those in which $R_2$ and $R_3$ are 2,6- or 2,4,6-substituted phenyl.

Preference is given to compounds of the formula I in which $R_2$ and $R_3$ are phenyl which is substituted by $C_1$–$C_4$alkoxy, in particular methoxy, and/or $C_1$–$C_4$alkyl, in particular methyl.

Other interesting compounds of the formula I are those in which $R_2$ and $R_3$ are phenyl which is substituted by $C_1$–$C_4$alkoxy, in particular methoxy.

The compounds according to the invention can be prepared, for example, by diacylation of a primary phosphine III by means of at least 2 equivalents of an acid chloride II in the presence of at least 2 equivalents of a base, and subsequent oxidation of the resultant diacylphosphine IV to give the phosphine oxide, in accordance with the following scheme:

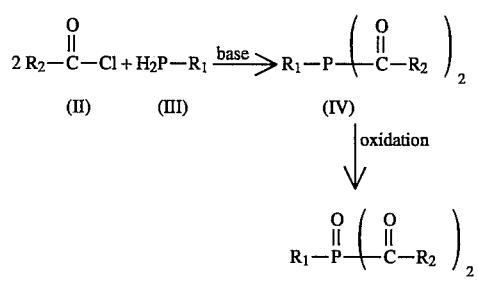

The asymmetrical compounds of the formula

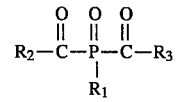

are obtained by employing one equivalent of an acid chloride (II) and one equivalent of

Examples of suitable bases are tertiary amines, alkali metals, lithium diisopropylamide, alkali metal alkoxides or alkali metal hydrides. The first reaction step is preferably carried out in solution. Suitable solvents are in particular hydrocarbons, for example alkanes, benzene, toluene or xylene. After the resultant base chloride has been separated off, the phosphine (IV) can be isolated by evaporation or the second reaction step is carded out with the solution of the crude product without isolation of (IV). Particularly suitable oxidants for the second step are hydrogen peroxide and organic peroxy compounds, for example peracetic acid, or air.

The primary phosphines (Ill) used as the starting material are known, in some cases commercially available compounds, or can be prepared analogously to known compounds (in this respect, see Houben-Weyl, Methoden der Org. Chemic [Methods of Organic Chemistry], XII/1, 60–63 (1963), G. Thieme-Verlag, Stuttgart). The acid chlorides of the formula (II) or (IIa) are also prepared by known methods from the prior art.

The compounds of the formula I can be used according to the invention as photoinitiators for the photopolymefisation of ethylenically unsaturated compounds or mixtures which contain such compounds. The unsaturated compounds may contain one or more olefinic double bonds. They may be of low molecular weight (monomeric) or relatively high molecular weight (oligomeric). Examples of monomers containing a double bond are alkyl or hydroxyalkyl acrylates or methacrylates, for example methyl, ethyl, butyl, 2-ethylhexyl and 2-hydroxyethyl acrylate, isobornyl acrylate, and methyl and ethyl methacrylate. Further examples of these monomers are acrylonitrile, acrylamide, methacrylamide, N-substituted (meth)acrylamides, vinyl esters, such as vinyl acetate, vinyl ethers, such as isobutyl vinyl ether, styrene, alkylstyrenes, halostyrenes, N-vinylpyrrolidone, vinyl chloride and vinylidene chloride.

Examples of monomers containing more than one double bond are ethylene glycol diacrylate, propylene glycol diacrylate, neopentyl glycol diacrylate, hexamethylene glycol diacrylate, bisphenol A diacrylate, 4,4'-bis(2-acryloyloxyethoxy)diphenylpropane, trimethylolpropane triacrylate, pentaerythritol triacrylate and tetraacrylate, pentaerythritol divinyl ether, vinyl acrylate, divinylbenzene, divinyl succinate, diallyl phthalate, triallyl phosphate, triallyl isocyanurate, tris(2-acryloylethyl)isocyanurate and divinyl ethers, for example triethylene glycol divinyl ether.

Examples of relatively high-molecular weight (oligomeric), polyunsaturated compounds are acrylated epoxy resins, acrylated polyethers, acrylated polyurethanes and acrylated polyesters. Further examples of unsaturated oligomers are unsaturated polyester resins, which are usually prepared from maleic acid, phthalic acid and one or more diols and have molecular weights of from about 500 to 3000. Unsaturated oligomers of this type are also known as prepolymers.

Two-component mixtures of a prepolymer with a polyunsaturated monomer or three-component mixtures which also contain a monounsaturated monomer are frequently used. The prepolymer here is primarily responsible for the properties of the coating film; variation of this prepolymer allows a person skilled in the art to modify the properties of the cured film. The polyunsaturated monomer functions as crosslinking agent which renders the coating film insoluble. The monounsaturated monomer functions as reactive thinner by means of which the viscosity is reduced without the need to use a solvent.

Two- and three-component systems of this type based on a prepolymer are used both for printing inks and for surface coatings, photoresists or other photocurable compositions.

Unsaturated polyester resins are usually used in two-component systems together with a monounsaturated monomer, preferably styrene. For photoresists, specific one-component systems are often used, for example polymaleimides, polychalcones or polyimides, as described in DE-A 2 308 830.

The unsaturated compounds may also be used in a mixture with non-photopolymerisable film-forming components. These may be, for example, physically drying polymers or solutions thereof in organic solvents, for example nitrocellulose or cellulose acetobutyrate. However, these may also be chemically or thermally curable resins, for example polyisocyanates, polyepoxides or melamine resins. The additional use of thermally curable resins is important for use in so-called hybrid systems, which are photopolymerised in a first step and crosslinked by thermal aftertreatment in a second step.

In addition to the photoinitiator, the photopolymerisable mixtures may contain various additives. Examples of these are thermal inhibitors, which are intended to prevent premature polymerisation, for example hydroquinone or stefi-cally hindered phenols. The shelf life in the dark can be extended by using, for example, copper compounds, phosphorus compounds, quaternary ammonium compounds or hydroxylamine derivatives. Atmospheric oxygen can be excluded during the polymerisation by addition of paraffin or similar wax-like substances, which migrate to the surface on commencement of the polymerisation. As light stabilisers, UV absorbers, for example those of the benzotriazole, benzophenone, hydroxyphenyl-s-triazine or oxalanilide type, can be added in small amounts. Still better is the addition of light stabilisers which do not absorb UV light, for example sterically hindered amines (HALS).

The photopolymerisation can be accelerated by adding amines, for example triethanolamine, N-methyldiethanolamine, ethyl p-dimethylaminobenzoate or Michler's ketone. The effect of the amines can be increased by adding aromatic ketones of the benzophenone type. The photopolymerisation can also be accelerated by adding photosensitisers, which shift or broaden the spectral sensitivity. These are, in particular, aromatic carbonyl compounds, for example derivatives of benzophenone, thioxanthone, anthraquinone and 3-acylcoumarin, and 3-(aroylmethylene)thiazolines.

Other conventional additives are—depending on the application—optical brighteners, fillers, pigments, dyes, wetting agents or flow-control agents.

The photoinitiators of the formula I according to the invention are particularly suitable for curing polymerisable compositions which contain substances which reduce the transparency.

Thick and pigmented coatings can be cured by addition of glass microbeads or powdered glass fibres, as described, for example, in U.S. Pat. No. 5 013 768.

The invention therefore also relates to photopolymerisable compositions comprising (a) at least one ethylenically unsaturated photopolymefisable compound and (b) at least one compound of the formula I as photoinitiator, it being possible for the composition furthermore to contain another photoinitiator and/or other additives.

The photopolymerisable compositions expediently contain the photoinitiator (b) in an amount of from 0.05 to 15% by weight, preferably from 0.2 to 5% by weight, based on the total solids content.

The invention also relates to compositions in which component (a) is at least one ethylenically unsaturated, photopolymerisable compound dissolved or emulsified in water.

Radiation-curable, aqueous prepolymer dispersions of this type are commercially available in many variations. This term is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymer in these compositions is in each case 100, to which are added the assistants and additives in various amounts, depending on the application.

The radiation-curable, water-dispersed, film-forming prepolymers, which are frequently also dissolved, are, for aqueous prepolymer dispersions, monofunctional or polyfunctional, ethylenically unsaturated prepolymers which are known per se, can be initiated by means of free radicals and contain, for example, from 0.01 to 1.0 mol of polymerisable double bonds per 100 g of prepolymer, and have a mean molecular weight of, for example, at least 400, in particular from 500 to 10,000. Depending on the application, however, prepolymers having higher molecular weights are also suitable. For example, polyesters containing polymerisable C—C double bonds and having a maximum acid number of 10, polyethers containing polymerisable C—C double bonds, hydroxyl-containing products of the reaction of a polyepoxide containing at least two epoxide groups per molecule with at least one α,β-ethylenically unsaturated carboxylic acid, polyurethane (meth)acrylates and α,β-ethylenically unsaturated acrylic copolymers containing acrylic radicals, as described in EP-A-12 339. Mixtures of these prepolymers may also be used. Also suitable are the polymerisable prepolymers described in EP-A-33 896, which are thioether adducts of polymerisable prepolymers having a mean molecular weight of at least 600, a carboxyl group content of from 0.2 to 15% and a content of from 0.01 to 0.8 mol of polymerisable C—C double bonds per 100 g of prepolymer. Other suitable aqueous dispersions based on specific alkyl (meth)acrylate polymers are described in EP-A-41 125, and suitable water-dispersible, radiation-curable prepolymers made from urethane acrylates are described in DE-A-2 936 039.

These radiation-curable, aqueous prepolymer dispersions may contain, as further additives, dispersion assistants, emulsifiers, antioxidants, light stabilisers, dyes, pigments, fillers, for example talc, gypsum, silica, rutile, carbon black, zinc oxide and iron oxides, reaction accelerators, flow-control agents, lubricants, wetting agents, thickeners, matting agents, antifoaming agents and other assistants which are conventional in surface-coating technology. Suitable dispersion assistants are water-soluble, high-molecular-weight organic compounds containing polar groups, for example polyvinyl alcohols, polyvinylpyrrolidone and cellulose ethers. Emulsifiers which can be used are nonionic emulsifiers, possibly also ionic emulsifiers.

In certain cases, it may be advantageous to use mixtures of two or more of the photoinitiators according to the invention. It is of course also possible to use mixtures with known photoinitiators, for example mixtures with benzophenone, acetophenone derivatives, benzoin ethers, benzil ketals, monoacylphosphine oxides, further bisacylphosphine oxides, peresters or titanocenes.

The invention therefore also relates to compositions in which the additional photoinitiators are compounds of the formula II

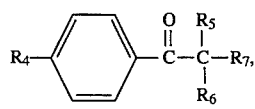
(II)

in which $R_4$ is hydrogen, $C_1$–$C_{18}$alkyl, $C_1$–$C_{18}$alkoxy, —OCH$_2$CH$_2$—OR$_8$, a

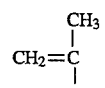

group or a

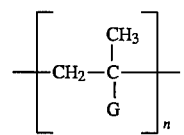

group, in which n has a value of from 2 to 10 and G is the

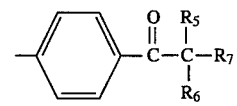

radical, $R_5$ and $R_6$, independently of one another, are hydrogen, $C_1$–$C_6$alkyl, phenyl, $C_1$–$C_{16}$alkoxy or —O(CH$_2$CH$_2$O)$_m$—$C_1$–$C_{16}$alkyl, in which m is a number from 1 to 20, or $R_5$ and $R_6$, together with the carbon atom to which they are bonded, form a cyclohexyl ring, $R_7$ is hydroxyl, $C_1$–$C_6$alkoxy or —O(CH$_2$CH$_2$O)$_m$—$C_1$–$C_{16}$alkyl, where $R_5$, $R_6$ and $R_7$ are not all simultaneously $C_1$–$C_{16}$alkoxy or —O(CH$_2$CH$_2$O)$_m$—$C_1$–$C_{16}$alkyl, and $R_8$ is hydrogen,

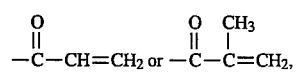

and/or of the formula III

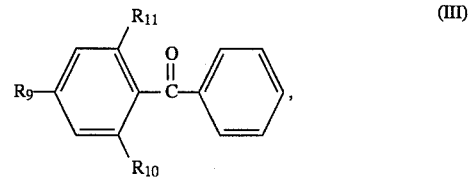
(III)

in which $R_9$, $R_{10}$ and $R_{11}$, independently of one another, are hydrogen or methyl, or mixtures thereof.

$C_1$–$C_{18}$Alkyl $R_4$ may be as defined for $R_1$. $C_1$–$C_6$Alkyl $R_5$ and $R_6$ and $C_1$–$C_4$alkyl $R_7$ may also be as defined for $R_1$, apart from the respective number of carbon atoms.

$C_1$–$C_{18}$Alkoxy $R_4$ is, for example, branched or unbranched alkoxy, for example methoxy, ethoxy, n-propoxy, isopropoxy, n-butoxy, isobutoxy, sec-butoxy, tert-butoxy, pentoxy, hexyloxy, heptyloxy, octyloxy, 2,4,4-trimethyl-1-pentoxy, 2-ethylhexyloxy, nonyloxy, decyloxy, dodecyloxy or octadecyloxy.

$C_1$–$C_{16}$Alkoxy $R_5$, $R_6$ and $R_7$ are as defined for $R_4$, apart from the corresponding number of carbon atoms. They are preferably decyloxy, methoxy or ethoxy, in particular methoxy or ethoxy.

The —O(CH$_2$CH$_2$O)$_m$—$C_1$–$C_{16}$alkyl radical represents 1 to 20 successive ethylene oxide units whose chain is terminated by a $C_1$–$C_{16}$alkyl radical. m is preferably 1 to 10, for example 1 to 8, in particular 1 to 6. The ethylene oxide unit chain is preferably terminated by a $C_1$–$C_{10}$alkyl radical, for example $C_1$–$C_8$alkyl radical, in particular a $C_1$–$C_4$alkyl radical.

Preference is given to compositions in which $R_5$ and $R_6$ in the formula II are, independently of one another, $C_1$–$C_6$alkyl, or, together with the carbon atom to which they are bonded, form a cyclohexyl ring, and $R_7$ is hydroxyl.

Further preferred compositions are those in which the proportion of compounds of the formula I in the mixture with compounds of the formulae II and/or III is from 5 to 95%, preferably from 30 to 70%.

Important compositions are also those in which $R_1$ in the compounds of the formula I is n-butyl, i-butyl or 2,4,4-trimethyl-1-pentyl, $R_2$ and $R_3$ are identical and are 2,6-dimethoxyphenyl or 2,4,6-trimethylphenyl, and $R_5$ and $R_6$ in the compounds of the formula II are identical and are methyl, and $R_7$ is hydroxyl or i-propoxy.

Preference is likewise given to compositions wherein compounds of the formula I in which $R_1$ is n-butyl, i-butyl or 2,4,4-trimethyl-1-pentyl, and $R_2$ and $R_3$ are identical and are 2,6-dimethoxyphenyl or 2,4,6-trimethylphenyl, and a mixture of compounds of the formula III comprising 20% of compounds of the formula III where $R_9$ and $R_{10}$ are hydrogen and $R_{11}$ is methyl and 80% of the compounds of the formula III in which $R_9$, $R_{10}$ and $R_{11}$ are methyl are present.

Particularly interesting compositions are those as described above which contain photoinitiator mixtures of the formulae I, II and/or III and which are liquid at room temperature.

The preparation of the compounds of the formulae II and III is known in general terms and some of the compounds are commercially available. The preparation of oligomeric compounds of the formula II is described for example, in EP-A-0 161 463. The preparation of compounds of the formula III is described, for example, in EP-A-209 831.

The photopolymerisable compositions can be used for various purposes, for example as printing inks, as varnishes, as white paints, for example for wood or metal, as coating compositions, inter alia for paper, wood, metal or plastic, as coloured pigmented paints, as daylight-curable coatings for buildings and road markings, for the preparation of clear or pigmented aqueous dispersions, for photographic reproduction processes, for image recording processes or for the production of printing plates which can be developed using organic solvents or aqueous-alkaline media, for the production of masks for screen printing, as dental filling materials, as adhesives, as etch or permanent resists and as solder stop masks for printed electronic circuits, for the production of three-dimensional articles by bulk curing (UV curing in transparent moulds) or by the stereolithography process, as described, for example, in U.S. Pat. No. 4,575,330, for the preparation of composite materials (for example styrenic polyesters, which may contain glass fibres and other assistants) and other thick-layer compositions, for the coating or encapsulation of electronic parts or as coatings for optical fibres.

The photocurable compositions according to the invention are suitable, for example, as coating materials for substrates of all types, for example wood, paper, ceramics, plastics, such as polyesters and cellulose acetate films, and metals, such as copper and aluminium, to which a protective coating or an image is to be applied by photopolymerisation. The substrates can be coated by applying a liquid composition, a solution or suspension to the substrate. This is accomplished, for example, by dipping, brushing, spraying or reverse-roll coating. The application rate (coating thickness) and the substrate type (coating base) depend on the desired area of application. Examples of coating bases for photographic information recording are polyester or cellulose acetate films or plastic-coated papers; coating bases for offset printing plates are specially treated aluminium, and coating bases for the production of printed circuits are copper-coated laminates. The coating thicknesses for photographic materials and offset printing plates are generally from about 0.5 to about 10 μm. If solvents are used, they are removed after the coating process.

Photocuring is of great importance for printing inks, since the drying time of the binder is a crucial factor for the speed of production of graphic products and should be in the order of fractions of seconds. UV-curable inks are of particular importance for offset printing.

The mixtures according to the invention are also highly suitable for the production of printing plates for flexographic or letterpress printing. Here, for example, mixtures of soluble linear polyamides or styrene-butadiene rubber with photopolymerisable monomers, for example acrylamides or acrylates, and a photoinitiator are used. Films and plates made from these systems (wet or dry) are exposed via the negative (or positive) of the printing master, and the uncured parts are subsequently eluted with a suitable solvent. Development can then be carried out in an organic solvent or in an aqueous-alkaline medium.

A further area of application of photocuring is the coating of metals, for example the coating of sheeting, tubes, cans or bottle caps, and the photocuring of plastics coatings, for example of PVC-based floor coverings or wall coverings.

An example of photocuring of coatings on paper is the colourless coating of labels, record sleeves or book covers.

Also important is the use of photocurable compositions for imaging processes and for the optical production of information carders. In these applications, the coating (wet or dry) applied to the base is exposed with short-wave light through a photomask, and the unexposed areas of the coating are removed by treatment with a solvent (=developer). The photocurable coating can also be applied by electrodeposition on metal. The exposed areas are crosslinked/polymeric and thus insoluble and remain on the base. If appropriate staining is carried out, visible images are formed. If the base is a metallised coating, the metal can be removed from the unexposed areas by etching after exposure and development or increased in thickness by electroplating. In this way, printed electronic circuits and photoresists can be produced.

The polymerisation is carried out by known methods of photopolymerisation by exposure to sunlight or to light which has a high short-wave content. Examples of suitable light sources are mercury medium-pressure, high-pressure and low-pressure lamps, superactinic fluorescent tubes, metal halide lamps or lasers whose emission maxima are in the range between 250 and 450 nm. Laser light sources have the advantage that photomasks are unnecessary, since the controlled laser beam writes directly on the photocurable coating. If a combination of photosensitisers is used, relatively long-wave light or laser beams up to 600 nm can also be used.

The invention also relates to a process for the photopolymerisation of compounds containing ethylenically unsaturated double bonds, which comprises exposing a composition as described above to light in the range from 200 to 600 nm.

The photoinitiators according to the invention have high reactivity, and coating surfaces having good gloss values are obtained when they are used. Due to the low tendency toward yellowing, the compounds according to the invention are particularly suitable for use in white paints, and their ability to cure thick coatings enables them to be used for the production of printing plates and composite materials. Storage of the cured compositions according to the invention in daylight enables their hardness to be further increased and the discoloration values to be further decreased.

The examples below serve to illustrate the invention further. Parts and percentages are by weight unless otherwise specified, both in the remainder of the description and in the patent claims. The abbreviation "calc." in the examples and tables indicates the calculated values in the elemental analyses.

EXAMPLE 1

Preparation of Bis(2,4,6-trimethylbenzoyl)isobutylphosphine Oxide 140.6 ml (0.225 mol, 1.6 M) of butyllithium are added dropwise under nitrogen at 0° C. over the course of 30 minutes to a solution of 31.9 ml (0.225 mol) of diisopropylamine in 80 ml of tetrahydrofuran. This solution is added dropwise at −30° C. over the course of 90 minutes to a solution of 41.1 g (0.225 mol) of 2,4,6-trimethylbenzoyl chloride and 12 ml (0.102 mol) of isobutylphosphine in 200 ml of tetrahydrofuran. After the mixture has been stirred for 2 hours at −30° C., the yellow solution is allowed to warm to room temperature and is washed once with water. The organic phase is dried using magnesium sulfate, filtered and evaporated on a rotary evaporator. The residue is dissolved in 200 ml of toluene, and 11.6 g (0.102 mol) of 30% hydrogen peroxide are added. After the mixture has been stirred for 2 hours, it is washed first with water then with saturated sodium hydrogen carbonate solution. The organic phase is then dried using magnesium sulfate and filtered, and the solution is evaporated on a rotary evaporator. Crystallisation from hexane gives 27.8 g (68.5% of theory) of the abovementioned compound as a yellow powder. The melting point is 85°–86° C.

Elemental analysis: calc. % C 72.34 found % C 72.13
calc. % H 7.84 found % H 7.94

EXAMPLE 2

Preparation of Bis(2,6-dimethoxybenzoyl)-n-butylphosphine Oxide

A mixture of 18 g (0.10 mol, 50% in toluene) of n-butylphosphine and 30.7 ml (0.22 mol) of triethylamine is added dropwise at 100°–110° C. over the course of 60 minutes to a solution of 44.1 g (0.22 mol) of 2,6-dimethoxybenzoyl chloride in 200 ml of toluene. After the mixture has been stirred at 100°–110° C. for 6 hours, the suspension which has formed is allowed to cool to room temperature and is diluted with toluene and washed first once with water then once with saturated sodium bicarbonate solution. 11.3 g (0.10 mol) of 30% hydrogen peroxide are added to the organic phase, and the mixture is stirred at 40° C. for 2 hours. The mixture is then washed with water and saturated sodium bicarbonate solution, and the organic phase is dried using magnesium sulfate, filtered and evaporated on a rotary evaporator. Crystallisation from ethyl acetate gives 30.2 g (69.6% of theory) of the abovementioned compound as a yellow powder. The melting point is 151°–152° C.

Elemental analysis: calc. % C 60.83 found % C 60.84
calc. % H 6.26 found % H 6.35

EXAMPLES 3–25

The compounds of Examples 3–25 are prepared analogously to the compound of Example 1 (=method A) or the compound of Example 2 (=method B) using the appropriately substituted benzoyl chlorides and phosphines. The compounds and their analytical data are shown in Table 1.

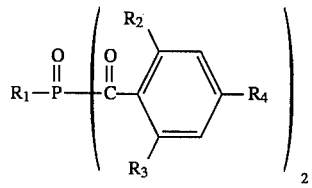

TABLE 1

| Ex. No. | $R_1$ | $R_2$ | $R_3$ | $R_4$ | Melting point [°C.] | Synthesis method | Elemental analysis [%] calc. found |
|---|---|---|---|---|---|---|---|
| 3 | $C_4H_9$ | $CH_3$ | $CH_3$ | $CH_3$ | 58 | A | C 72.34 H 7.84 / 72.08 8.01 |
| 4 | $CH(CH_3)C_2H_5$ | $CH_3$ | $CH_3$ | $CH_3$ | 115 | A | C 72.34 H 7.84 / 72.23 7.93 |
| 5 | $C(CH_3)_3$ | $CH_3$ | $CH_3$ | $CH_3$ | 160 | A | C 72.34 H 7.84 / 72.21 8.06 |
| 6 | cyclohexyl | $CH_3$ | $CH_3$ | $CH_3$ | 140 | A | C 73.56 H 7.84 / 73.39 8.06 |
| 7 | $C_8H_{17}$ | $CH_3$ | $CH_3$ | $CH_3$ | resin | A | C 73.98 H 8.65 / 73.83 8.89 |
| 8 | $CH_2CH(CH_3)CH_2C(CH_3)_3$ | $CH_3$ | $CH_3$ | $CH_3$ | resin | A | C 73.98 H 8.65 / 73.97 8.98 |
| 9 | $CH_2CH(CH_3)_2$ | $OCH_3$ | $OCH_3$ | H | 183 | B | C 60.83 H 6.26 / 60.70 6.09 |
| 10 | $CH(CH_3)C_2H_5$ | $OCH_3$ | $OCH_3$ | H | 159 | B | C 60.83 H 6.26 / 60.75 6.24 |
| 11 | $C(CH_3)_3$ | $OCH_3$ | $OCH_3$ | H | 235 | B | C 60.83 H 6.26 / 60.00 6.17 |
| 12 | cyclohexyl | $OCH_3$ | $OCH_3$ | H | 165 | B | C 62.60 H 6.35 / 62.40 6.39 |
| 13 | $C_8H_{17}$ | $OCH_3$ | $OCH_3$ | H | 118 | B | C 63.66 H 7.19 / 63.36 7.22 |
| 14 | $CH_2CH(CH_3)CH_2C(CH_3)_3$ | $OCH_3$ | $OCH_3$ | H | 117 | B | C 63.06 H 7.19 / 63.60 7.04 |
| 15 | $CH(CH_3)C_2H_5$ | $OC_2H_5$ | $OC_2H_5$ | H | resin | B | C 63.66 H 7.19 / 62.47 7.33 |
| 16 | $CH_2CH(CH_3)_2$ | $OC_2H_5$ | $OC_2H_5$ | H | 110 | B | C 63.66 H 7.19 / 63.54 7.02 |
| 17 | $CH_2CH(CH_3)_2$ | $OC_4H_9$ | $OC_4H_9$ | H | 70 | B | C 67.75 H 8.53 / 67.35 8.49 |

TABLE 1-continued

| Ex. No. | R$_1$ | R$_2$ | R$_3$ | R$_4$ | Melting point [°C.] | Synthesis method | Elemental analysis [%] calc. found | | |
|---|---|---|---|---|---|---|---|---|---|
| 18 | CH$_2$CH(CH$_3$)$_2$ | CH$_3$ | CH$_3$ | H | 54 | A | C 71.33 71.32 | H 7.35 7.54 | |
| 19 | CH$_2$CH(CH$_3$)$_2$ | CH$_3$ | OCH$_3$ | OCH$_3$ | 161 | B | C 62.33 62.23 | H 6.76 6.76 | |
| 20 | CH$_2$CH(CH$_3$)$_2$ | OCH$_3$ | H | H | 175 | B | C 62.33 62.29 | H 6.76 6.86 | |
| 21 | CH(CH$_3$)C$_2$H$_5$ | OCH$_3$ | H | H | 153 | B | C 62.33 62.10 | H 6.76 6.70 | |
| 22 | CH$_2$CH(CH$_3$)$_2$ | Cl | Cl | H | 153 | B | C 47.82 47.74 | H 3.34 3.25 | Cl 31.37 31.28 |
| 23 | CH(CH$_3$)C$_2$H$_5$ | Cl | Cl | H | 136 | B | C 47.82 47.41 | H 3.34 3.53 | Cl 31.37 30.62 |
| 24 | cyclohexyl | Cl | Cl | H | 182 | B | C 50.24 50.56 | H 3.58 3.90 | Cl 29.66 29.52 |
| 25 | C$_8$H$_{17}$ | Cl | Cl | H | 100 | B | C 51.99 51.87 | H 4.56 4.63 | Cl 27.90 27.89 |
| 26 | CH$_2$CH(CH$_3$)$_2$ | OCH$_3$ | OCH$_2$CH$_3$ | H | 174–175 | B | C 62.33 62.29 | H 6.76 6.86 | |
| 27 | CH(CH$_3$)C$_2$H$_5$ | OCH$_3$ | OCH$_2$CH$_3$ | H | 152–153 | B | C 62.33 62.10 | H 6.76 6.70 | |
| 28 | CH$_2$CH(CH$_3$)CH$_2$C(CH$_3$)3 | CH$_3$ | CH$_3$ | H | resin | A | C 73.21 73.15 | H 8.27 8.47 | |
| 29 | C$_4$H$_9$ | CH$_3$ | CH$_3$ | OC$_4$H$_9$ | oil | A | C 70.02 69.93 | H 8.42 8.65 | |
| 30 | C$_4$H$_9$ | CH$_3$ | CH$_3$ | OCH$_3$ | oil | A | C 66.96 67.01 | H 7.26 7.32 | |
| 31 | C$_4$H$_9$ | CH$_3$ | CH$_2$CH$_3$ | OCH$_3$ | oil | A | C 68.11 68.09 | H 7.69 7.76 | |
| 32 | C$_4$H$_9$ | CH$_3$ | CH$_2$CH$_2$CH$_3$ | OCH$_3$ | oil | A | C 69.12 68.73 | H 8.08 8,18 | |
| 33 | C$_4$H$_9$ | CH$_3$ | OC$_4$H$_9$ | OC$_4$H$_9$ | 68–69 | B | C 68.55 68.21 | H 8.79 8.80 | |
| 34 | CH$_2$CH(CH$_3$)CH$_2$C(CH$_3$)$_3$ | CH$_3$ | OC$_4$H$_9$ | OC$_4$H$_9$ | oil | B | C 69.94 69.37 | H 9.24 9.50 | |
| 35 | C$_4$H$_9$ | Cl | Cl | H | 151–153 | B | C 47.82 47.85 | H 3.34 3.35 | Cl 31.37 31.02 |
| 36 | C(CH$_3$)$_3$ | Cl | Cl | H | 209–213 | B | 0 47.82 47.83 | H 3.34 2.92 | Cl 31.37 31.47 |
| 37 | CH$_2$CH(CH$_3$)CH$_2$C(CH$_3$)$_3$ | Cl | Cl | H | 127–128 | B | C 51.99 51.75 | H 4.56 4.53 | Cl 27.90 27.56 |
| 38 | C$_{18}$H$_{37}$ | OCH$_3$ | OCH$_3$ | H | 84 | B | C 68.55 68.20 | H 8.79 8.83 | |

EXAMPLE 39

Preparation of 2,6-dimethoxybenzoyl-2,4,6-trimethylbenzoyl-n-butylphosphine Oxide A mixture of 9.0 g (0.05 mol, 50% in toluene) of n-butylphosphine and 10.1 g (0.10 mol) of triethylamine is added dropwise under nitrogen at 100°–110° C. over the course of 10 minutes to a solution of 9.1 g (0.05 mol) of 2,4,6-trimethylbenzoyl chloride in 100 ml of toluene. After the mixture has been stirred at 100°–110° C. for 3 hours, a solution of 10 g (0.05 mol) of 2,6-dimethylbenzoyl chloride in 50 ml of toluene is added dropwise over the course of 30 minutes at the same temperature. After the mixture has been stirred at 100°–110° C. for a further 5 hours, the yellowish suspension which has formed is allowed to cool to room temperature and is washed once with water and once with sodium bicarbonate. 5.7 g (0.05 mol) of 30% hydrogen peroxide are added to the organic phase, and the mixture is stirred at 60° C. for 2 hours. The mixture is then washed with water and saturated sodium bicarbonate solution, and the organic phase is dried using magnesium sulfate, filtered and evaporated on a rotary evaporator. Purification by chromatography (eluent:hexane/ethyl acetate 1:1) and subsequent crystallisation from cyclohexane give 1.80 g (8.7% of theory) of the title compound as a yellow powder having a melting point of 94°–96° C.

Elemental analysis: calc. % C 66.33 found % C 65.61 calc. % H 7.02 found % H 7.04

EXAMPLE 40

Photoinitiator Reactivity in a White Paint

The photoinitiators are incorporated in concentrations of 0.5 and 1% by weight into a white paint formulation comprising:

67.5 parts of ®Ebecryl 830 (polyester acrylate from UCB, Belgium)

5.0 parts of hexanediol diacrylate 2.5 parts of trimethylolpropane triacrylate and 25.0 parts of titanium dioxide (R-TC2) of the rutile type.

The samples are applied to chipboard using a 100 µm hand coater and cured using an 80 W/cm mercury medium-pressure lamp (Hanovia type) at a belt speed of 10 m/min. The number of passes until the wipe strength is reached is determined. The König pendulum hardness (DIN 53157) is measured on the white paint coats cured in this way immediately after the curing. The coatings are then exposed further under four 40 W lamps (Philips TL 03), and the pendulum hardness is re-measured after 15 minutes and 16 hours. The yellowness index is measured in accordance with ASTM D 1925-70 after 16 hours.

The pendulum hardness and the wipe strength are measures of the reactivity of the tested photoinitiator; the lower the number of passes before the wipe strength is reached and the higher the pendulum hardness values, the more reactive the photocuring agent. The yellowness index values are a measure of the yellowing; the lower the values, the less the yellowing of the tested formulation.

The measurement results are shown in Table 2 below.

TABLE 2

| Compound from Ex. | Concentration [% by wt.] | Number of passes [10 m/min] | Pendulum hardness immediately | Pendulum hardness after 15 min | Pendulum hardness after 16 h | Yellowness Index after 16 h |
|---|---|---|---|---|---|---|
| 4 | 0.5 | 5 | 165 | 179 | 185 | 1.2 |
|   | 1.0 | 3 | 164 | 182 | 197 | 1.2 |
| 7 | 0.5 | 6 | 164 | 169 | 178 | 1.1 |
|   | 1.0 | 4 | 178 | 184 | 199 | 1.2 |
| 13 | 0.5 | 6 | 157 | 160 | 174 | 1.4 |
|    | 1.0 | 4 | 158 | 172 | 186 | 1.6 |

EXAMPLE 41

Photoinitiator Reactivity in a White Paint

A white paint is prepared from 75 parts of a formulation of 99.5% of Roskydal UV 502 A (BAYER, Germany), 0.5% of Byk 300 (Byk-Mallinckrodt) and 25 parts of titanium dioxide. The photoinitiators are incorporated in the stated concentrations by shaking with beads (for 2% by weight of photoinitiator) or by stirring at 50° C. (for 1.5% by weight of photoinitiator). The formulation is then applied to chipboard using a 150 μm hand coater, and the coating is preexposed for 1.5 minutes under four 40 W lamps (Philips TL 03). The further curing is carried out in two exposure variants: a) the samples are exposed twice under one 80 W/cm mercury medium-pressure lamp (Hanovia type) at a belt speed of m/min. b) The samples are cured twice under one 120 W/cm Fusion D and one 80 W/cm mercury medium-pressure lamp (Hanovia type) arranged one after the other, at a belt speed of 3 m/min.

The König pendulum hardness (DIN 53157) is measured on the cured coatings immediately, after 15 minutes and after 16 hours of further exposure under 40 W lamps (Philips TL 03). The higher the values, the better cured the formulation. The yellowing (yellowness index, YI) of the coatings is determined in accordance with ASTM D 1925-70 after further exposure for 16 hours. The lower the values, the less the yellowing of the coating. The results of exposure variant a) are shown in Table 3. The results of exposure variant b) are shown in Table 4.

TABLE 3

(Exposure variant a))

| Compound from Ex. | Concentration [% by wt.] | Pendulum hardness immediately | Pendulum hardness after 15 min | Pendulum hardness after 16 h | Yellowness Index after 16 h |
|---|---|---|---|---|---|
| 4 | 1.5 | 108 | 130 | 179 | 1.0 |
|   | 2.0 | 115 | 147 | 179 | 1.0 |
| 6 | 1.5 | 113 | 130 | 182 | 0.8 |
|   | 2.0 | 120 | 154 | 188 | 1.0 |

TABLE 4

(Exposure variant b))

| Compound from Ex. | Concentration [% by wt.] | Pendulum hardness immediately | Pendulum hardness after 15 min | Pendulum hardness after 16 h | Yellowness Index after 16 h |
|---|---|---|---|---|---|
| 4 | 1.5 | 150 | 153 | 179 | 1.1 |
|   | 2.0 | 160 | 165 | 167 | 1.1 |
| 6 | 1,5 | 151 | 158 | 181 | 1.0 |
|   | 2,0 | 165 | 170 | 176 | 1.1 |

EXAMPLE 42

Photoinitiator Reactivity in a White Paint

A photopolymerisable composition is prepared from:

13.5 parts of ®Ebecryl 830 (polyester acrylate from UCB, Belgium)

0.5 part of trimethylolpropane triacrylate (Degussa)

1.0 part of 1,6-hexanediol diacrylate (Röhm)

5.0 parts of titanium dioxide (rutile type, ®R-TC 2 from Tioxide, France).

Mixtures of the photoinitiator from Example 14 (A) with 1-benzoyl-1hydroxy-1-methylethane (B) in the amounts shown in Table 5 are mixed with this composition. The formulation is applied to aluminium sheeting in a coating thickness of 100 μm, and the resultant samples are exposed to a mercury medium-pressure lamp (80 W/cm, Hanovia type). During this exposure, the samples are passed under the lamp on a belt moving at a speed of 10 m/min until a wipe-resistant paint coat has formed. The lower the number of passes (n), the better the action of the tested photoinitiator or photoinitiator mixtures. The yellowing of the samples is determined in accordance with ASTM D 1925-70 as the yellowness index. The lower the value, the less the yellowing of the sample. The yellowing is measured immediately after curing, after additional exposure of 15 minutes and 16 hours under four TL 40/03 lamps (40 W, Philips). The results are shown in Table 5.

TABLE 5

| Compound | Concentration [% by wt.] | Number of passes [10 m/min] | Yellowness Index immediately | Yellowness Index after 15 min | Yellowness Index after 16 h |
|---|---|---|---|---|---|
| A | 0.5 | 8 | 1.0 | 1.0 | −0.7 |
| A | 1.0 | 5 | 1.9 | 2.3 | −0.5 |
| A | 1.5 | 4 | 3.3 | 4.2 | −0.1 |
| A | 2.0 | 3 | 4.1 | 5.9 | −0.2 |
| A | 0.5 | 4 | 0.8 | 1.0 | −1.2 |
| B | 0.5 | | | | |
| A | 0.75 | 3 | 1.6 | 1.7 | −0.6 |
| B | 0.75 | | | | |
| A | 1.0 | 2 | 1.8 | 3.1 | −0.8 |
| B | 1.0 | | | | |
| A | 0.65 | 4 | 1.3 | 1.6 | −0.9 |
| B | 0.35 | | | | |
| A | 1.0 | 3 | 1.1 | 0.8 | −1.4 |
| B | 0.5 | | | | |
| A | 1.3 | 2 | 2.9 | 4.2 | −0.2 |
| B | 0.7 | | | | |
| A | 0.35 | 4 | 0.8 | 0.7 | −0.8 |
| B | 0.65 | | | | |
| A | 0.5 | 4 | 0.7 | 0.8 | −1.2 |
| B | 1.0 | | | | |
| A | 0.7 | 2 | 1.9 | 2.2 | −0.6 |
| B | 1.3 | | | | |

EXAMPLE 43

Photoinitiator Reactivity in a White Paint

A photopolymerisable composition is prepared from:

99.5 parts of ®Roskydal UV 502 A (UPES/styrene solution; BAYER; contains 35% of styrene and 25% of rutile titanium dioxide) 0.5 part of ®Byk 300 (flow-control agent, Byk-Mallinckrodt).

The initiator mixtures (C) [=50% of the photoinitiator from Example 14+50% of 1-benzoyl-1-hydroxy-1-methylethane] and (D) [=33% of the photoinitiator from Example 14+67% of 1-benzoyl-1-hydroxy-1-methylethane] in the amounts shown in Table 6 are mixed with this composition. The formulation is applied to chipboard in a coating thickness of 150 μm and cured under various exposure conditions.

1) The samples are preexposed for 1.5 minutes under 4 tl 40/04 lamps (40 W, Philips). Curing is then carried out under one 80 W/cm mercury medium-pressure lamp by passing the sample under the lamp once at a speed of 3 m/min.

2) The curing is carried out by passing the samples, without preexposure, once under 2 80 W/cm mercury medium-pressure lamps at a speed of 3 m/min.

The assessment criteria used are the König pendulum hardness (DIN 53157), the yellowness index in accordance with ASTM D 1925-70 and the gloss at 20° and 60°. The results are shown in Table 6.

TABLE 6

| Photo-initiator | Amount [% by wt.] | Pendulum hardness | Yellowness Index | Gloss [20/60°] |
|---|---|---|---|---|
| 1) with preexposure ||||||
| C | 2 | 93 | 2.3 | 84/92 |
| C | 4 | 91 | 3.6 | 84/92 |
| D | 2 | 75 | 2.2 | 84/92 |
| D | 4 | 92 | 2.9 | 84/92 |
| 2) without preexposure ||||||
| C | 4 | 117 | 4.1 | 86/93 |
| D | 4 | 102 | 3.5 | 86/93 |

EXAMPLE 44

Photoinitiator Reactivity in a Varnish

The photoinitiators in the concentrations shown in Table 7 are dissolved in 100 parts of ®Roskydal 502 (unsaturated polyester resin, dissolved to about 80% in butyl acetate, from BAYER). The photoinitiators from Examples 1 and 22, and 2,2-dimethoxy-1,2-diphenylethan-1-one (=E) are used. The formulations are applied to chipboard in a coating thickness of 100 μm, and the coatings are dried for 1 minute at 50° C. The curing is carried out by exposure using two 80 W/cm mercury medium-pressure lamps by passing the samples under the lamps at a belt speed of 20 m/min. In order to determine the reactivity, the number of passes is measured which is necessary to achieve a wipe-resistant surface (=n). In addition, the König pendulum hardness (DIN 53157) and the yellowness index in accordance with ASTM D 1925-70 of the samples are measured. The pendulum hardness is additionally measured after n+1 exposure passes of the samples. The results are shown in Table 7.

TABLE 7

| Photo-initiator from Example | Amount [% by wt.] | Number of passes (n) [20 m/min] | Pendulum hardness after n | Pendulum hardness after n + 1 | Yellowness Index |
|---|---|---|---|---|---|
| E | 2 | 2 | 69 | 91 | 7.2 |
| 1 | 2 | 2 | 124 | 134 | 8.3 |
| 22 | 2 | 3 | 81 | 112 | 7.8 |
| E | 1.25 | 2 | 139 | 148 | 7.5 |
| 1 | 0.75 | | | | |
| E | 1.25 | 2 | 127 | 132 | 6.9 |
| 22 | 0.75 | | | | |

EXAMPLE 45

Production of a Flexographic Printing Plate a) 1.13 parts of ®Irganox 565 (antioxidant; Ciba-Geigy, Switzerland), 0.03 part of ®Ceres Black (pigment, Sudan Black No. 86015; Fluka, Switzerland) and 0.6% of the photoinitiator to be tested are dissolved in 41.54 parts of 1,6-hexanediol diacrylate (HDDA) at a maximum of 50° C. with stiffing for 30 minutes. 332.30 parts of ®Cariflex TR 1107 (block polymer made from polyisoprene and polystyrene; Shell Chemie, Holland) are melted with 2 g of excess for 10 minutes at 140° C. on the calender to give a sheeted-out compound. The dropwise addition of the previously prepared HDDA solution is begun at 110° C. The dropwise addition takes about 15 minutes. The entire formulation is then homogenised on the calender at 100° C. for a further 15 minutes. After removal from the calender, the crude sheeted-out compound is placed between two Teflon films and cooled in a water-cooled press at a pressure of 100 kp/cm². 70 g of the sheeted-out compound are enclosed between two 76 μm polyester films in a 2 mm thick press frame and pressed to give sheets 2 mm in thickness by heating the sandwich first for one minute without using pressure between the surfaces of a second press preheated to 90° C. and then pressing the sandwich for 10 minutes at a pressing pressure of 200 kp/cm². The sandwich is then cooled in the first press, which is water-cooled to 15° C., for 10 minutes at a pressing pressure of 200 kp/cm² and is subsequently cut out of the pressing frame.

b) In order to determine the optimum exposure time for base formation of the plate covered on both sides with polyester film, a strip measuring 4×24 cm is cut out. This strip is exposed stepwise in a BASF Nyloprint exposure unit fitted with 20 W Nyloprint 2051 tubes by moving a mask between 9 exposure steps each lasting 20 seconds. This produces on the strip a curing pattern comprising 10 sections corresponding to the exposure times 0, 20, 40, 60, 80, 100, 120, 140, 160 and 180 seconds. The plate is rotated and a 1.5 cm broad central strip is covered in the longitudinal direction. The entire structure is covered by a thin UV-transparent film, sucked against the exposure stage by means of a vacuum and exposed for 6 minutes. The exposed plate is developed by washing out the insufficiently crosslinked areas in a BASF Nyloprint circular washer at 20° C. using a washing solution comprising a 4:1 mixture of tetrachloroethylene and n-butanol. The plate is dried for 1 hour at 80° C. in a fan-assisted oven, left for 5 minutes, dipped in a 0.4% bromine solution for fixing and dipped for 10 seconds in an aqueous solution of 1.15% sodium thiosulfate/sodium carbonate for neutralisation. The plate is then rinsed with demineralised water for 30 seconds. The central strip of the plate treated in this way is evaluated. The exposure time which results in the formation of a 1400 μm base (=reverse side exposure time) is determined.

c) A piece of a plate sandwich produced as under a) is exposed over the entire surface for the exposure time determined under b) in order to form a plate base. The plate is then rotated, the polyester film is removed and a test negative having 4 fields is applied. Exposure of the 4 test fields of the test negative is carried out in steps using a movable mask. The first field is exposed for 6 minutes, and the exposure time of fields 2–4 is increased by one minute from field to field. The plate is developed and fixed as described above. The plate is then exposed over the entire surface on both sides for a further 6 minutes. The exposure time for achieving a shade value of 2% (=front side exposure time) is determined. The results are shown in Table 8.

TABLE 8

| Compound from Ex. | Reverse side exposure time [s] | Front side exposure time to shade value = 2% [min] |
|---|---|---|
| 1 | 80 | 7 |
| 8 | 80 | 8 |

What is claimed is:
1. A composition comprising

(a) at least one ethylenically unsaturated photopolymerizable compound; and
(b) at least one compound of the formula I

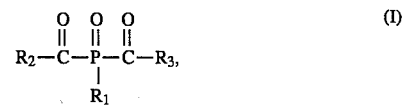

in which $R_1$ is $C_{14}C_{18}$alkyl, cyclopentyl or cyclohexyl, and $R_2$ and $R_3$, independently of one another, are phenyl which is unsubstituted or carries 1, 2, 3 or 4 substituents selected from the group consisting of $C_1$–$C_4$alkyl, $C_1$–$C_4$alkoxy or a mixture thereof, as photoinitiator.

2. A composition according to claim 1, in which $R_2$ and $R_3$ are identical.

3. A composition according to claim 2, in which $R_1$ is $C_1$–$C_{18}$alkyl or cyclohexyl, and $R_2$ $R_3$ are phenyl carrying 1, 2, 3 or 4 substituents selected from the group consisting of $C_1$–$C_4$alkyl and $C_1$–$C_4$alkoxy.

4. A composition according to claim 3, in which $R_1$ is $C_4$–$C_8$alkyl or cyclohexyl.

5. A compound according to claim 2, in which $R_2$ and $R_3$ are 2,6- or 2,4,6-substituted phenyl.

6. A composition according to claim 2, in which $R_2$ and $R_3$ are phenyl which is substituted by $C_1$–$C_4$alkoxy, $C_1$–$C_4$alkyl or a mixture thereof.

7. A composition according to claim 6, in which $R_2$ and $R_3$ are phenyl which is substituted by $C_1$–$C_4$alkyl.

8. A composition according to claim 6, in which $R_2$ and $R_3$ are phenyl which is substituted by methyl.

9. A composition according to claim 1, in which component (b) is present in an amount of from 0.05 to 15% by weight, based on the total solids content of the composition.

10. A composition according to claim 1, in which other photoinitiatiors and/or additives are present in addition to component (b).

11. A composition according to claim 10, in which the additional photoinitiators are compounds of the formula II

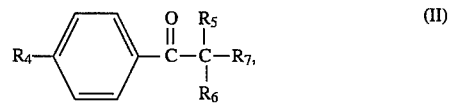

in which $R_4$ is hydrogen, $C_1$–$C_{18}$alkyl, $C_1$–$C_{18}$alkoxy, —OCH$_2$CH$_2$—OR$_8$, a

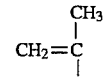

group or a

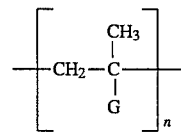

group, in which n has a value of from 2 to 10 and G is the

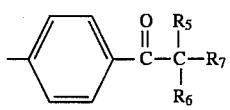

radical;

R$_5$ and R$_6$, independently of one another, are hydrogen, C$_1$–C$_6$alkyl, phenyl, C$_1$–C$_{16}$alkoxy or —O(CH$_2$CH$_2$O)$_m$'C$_1$–C$_{16}$alkyl, in which m is a number from 1 to 20, or R$_5$ and R$_6$, together with the carbon atom to which they are bonded, form a cyclohexyl ring; R$_7$ is hydroxyl, C$_1$–C$_6$alkoxy or —O(CH$_2$CH$_2$O)$_m$—C$_1$—C$_{16}$alkyl; and R$_8$ is hydrogen,

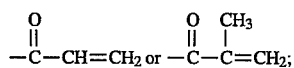

provided that R$_5$, R$_6$ and R$_7$ are not all simultaneously C$_1$–C$_{16}$alkoxy or —O(CH$_2$CH$_2$O)$_m$—C$_1$–C$_{16}$alkyl; and/or compounds of the formula III

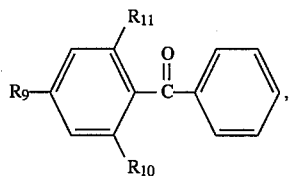

in which R$_9$, R$_{10}$ and R$_{11}$, independently of one another, are hydrogen or methyl; or mixtures thereof.

12. A composition according to claim 11, in which R$_5$ and R$_6$ in the formula II are, independently of one another, C$_1$–C$_6$alkyl, or together with the carbon atom to which they are bonded, form a cyclohexyl ring, and R$_7$ is hydroxyl.

13. A composition according to claim 11, in which the proportion of compounds of the formula I in the mixture with compounds of the formula II and/or III is from 5 to 95%.

14. A composition according to claim 11, in which R$_1$ in the compounds of the formula I is n-butyl, i-butyl or 2,4,4-trimethyl-1-pentyl, R$_2$ and R$_3$ are identical and are 2,6-dimethoxyphenyl or 2,4,6-trimethylphenyl, and R$_5$ and R$_6$ in the compounds of the formula II are identical and are methyl, and R$_7$ is hydroxy or i-propoxy.

15. A composition according to claim 11, wherein compounds of the formula I in which R$_1$ is n-butyl, i-butyl or 2,4,4-trimethyl-1-pentyl, and R$_2$ and R$_3$ are identical and are 2,6-dimethoxyphenyl or 2,4,6-trimethylphenyl, and a mixture of compounds of the formula III comprising 20% of compounds of the formula III where R$_9$ and R$_{10}$ are hydrogen and R$_{11}$ is methyl and 80% of compounds of the formula III in which R$_9$, R$_{10}$ and R$_{11}$ are methyl, are present.

* * * * *